United States Patent
Huber et al.

(10) Patent No.: US 12,419,992 B2
(45) Date of Patent: Sep. 23, 2025

(54) CARTILAGE MATRIX

(71) Applicant: LifeNet Health, Virginia Beach, VA (US)

(72) Inventors: Alexander Huber, Chesapeake, VA (US); Paresa Taghavie-Moghadam, Virginia Beach, VA (US)

(73) Assignee: Matney Legal Group PLLC, Virginia Beach, VA (US)

( * ) Notice: Subject to any disclaimer, the term of this patent is extended or adjusted under 35 U.S.C. 154(b) by 492 days.

(21) Appl. No.: 16/631,942

(22) PCT Filed: Jul. 20, 2018

(86) PCT No.: PCT/US2018/043144
§ 371 (c)(1),
(2) Date: Jan. 17, 2020

(87) PCT Pub. No.: WO2019/018800
PCT Pub. Date: Jan. 24, 2019

(65) Prior Publication Data
US 2020/0222588 A1 Jul. 16, 2020

Related U.S. Application Data

(60) Provisional application No. 62/535,151, filed on Jul. 20, 2017.

(51) Int. Cl.
*A61L 27/36* (2006.01)
*A61L 27/38* (2006.01)

(52) U.S. Cl.
CPC ....... *A61L 27/3612* (2013.01); *A61L 27/3687* (2013.01); *A61L 27/3817* (2013.01);
(Continued)

(58) Field of Classification Search
None
See application file for complete search history.

(56) References Cited

U.S. PATENT DOCUMENTS

| | | | |
|---|---|---|---|
| 7,824,711 B2 | 11/2010 | Kizer et al. | |
| 8,318,212 B2 | 11/2012 | Malinin | |

(Continued)

FOREIGN PATENT DOCUMENTS

| | | |
|---|---|---|
| CN | 102188748 A | 9/2011 |
| WO | 2016024025 A1 | 2/2016 |
| WO | 2017008035 A1 | 1/2017 |

OTHER PUBLICATIONS

Su et al. (Development of porous medical implant scaffolds via laser additive manufacturing), Transaction of Nonferrous Metals Society of China, 22(2012) s181-s187 (Year: 2012).*

(Continued)

*Primary Examiner* — Isis A Ghali
(74) *Attorney, Agent, or Firm* — Matney Legal Group PLLC

(57) ABSTRACT

The present invention provides a cartilage matrix having a high decellularization level and a low glycosaminoglycan (GAG) content. The cartilage matrix exhibits desirable characteristics, for example, cohesiveness, tackiness and malleability, for use in cartilage repair. Also provided is a method of preparing the cartilage matrix, comprising decellularizing a cartilage to generate a decellularized cartilage, and deglycosylating the decellularized cartilage.

16 Claims, 9 Drawing Sheets

(52) U.S. Cl.
CPC ....... *A61L 27/3852* (2013.01); *A61L 27/3895* (2013.01); *A61L 2300/406* (2013.01); *A61L 2300/414* (2013.01)

(56) References Cited

U.S. PATENT DOCUMENTS

| | | | |
|---|---|---|---|
| 9,186,380 B2 | 11/2015 | Shi et al. | |
| 2004/0112781 A1* | 6/2004 | Hofverberg | A61C 8/0087 206/363 |
| 2007/0014773 A1 | 1/2007 | Matheny et al. | |
| 2007/0082058 A1* | 4/2007 | Masinaei | A61L 27/3604 424/549 |
| 2009/0024223 A1 | 1/2009 | Chen et al. | |
| 2009/0024229 A1 | 1/2009 | Chen et al. | |
| 2010/0119577 A1 | 5/2010 | Min et al. | |
| 2013/0338792 A1 | 12/2013 | Schmieding et al. | |
| 2014/0341964 A1* | 11/2014 | McKay | A61L 24/0084 514/8.8 |
| 2016/0235892 A1 | 8/2016 | Detamore et al. | |

OTHER PUBLICATIONS

Erten et al. (Detergent-free decellularization of bovine costal cartilage for chondrogenic differentiation of human adipose mesenchymal stem cells in vitro), Royal Society of Chemistry, 2016, 6, 94236-94246 (Year: 2016).*
Wang et al. (Endogenous regeneration of critical-size chondral defect in immunocompromised rat xiphoid cartilage using decellularized human bone matrix scaffolds), Tissue engineering Part A, vol. 18, Nov. 21 and 22, (Year: 2012).*
Cheng et al. "Decellularized and cell-derived extracellular matrices as scaffolds for orthopaedic tissue engineering", Biotechnology Advances, 32, 462-484 (Year: 2014).*
Gupta et al. "Microsphere-based osteochondral scaffolds carrying opposing gradients of decellularized cartilage and demineralized bone matrix", Biomaterials Science & Engineering 1955-1963 (Year: 2016).*
"Demineralized Bone Definition", Spine Health (Year: 1999).*
Tofighi et al. "New cartilage of synthetic, bioresorbable and injectable calcium phosphate bone substitute materials: alpha-bsm, beta-bsm and gamma-bsm", Journal of Biomimetics, Biomaterial and Tissue Engineering, ISSN, 1662-100X, vol. 2, pp. 39-55 (Year: 2009).*
International Preliminary Report on Patentability for International Application No. PCT/US2018/043144, dated Jan. 21, 2020, 5 pages.
International Search Report and Written Opinion for International Application PCT/US2018/043144, dated Oct. 15, 2018, 7 pages.
Kheir, E., et al., "Development and characterization of an acellular porcine cartilage bone matrix for use in tissue engineering." Journal of Biomedical Materials Research Part A, vol. 99A(2), Nov. 19, 2011, pp. 283-294, XP055217527.
Schneider, C., et al., "Systematic comparison of protocols for the preparation of human articular cartilage for use as scaffold material in cartilage tissue engineering." Tissue Engineering: Part C, vol. 22(12), Dec. 1, 2016, pp. 1095-1107, XP009522615, Retrieved from the Internet: https://www.liebertpub.com/doi/abs/10.1089/ten.TEC.2016.0380.
Extended European Search Report for European Application No. 18 835 229.8, dated Mar. 15, 2021, 12 pages.
Axelsson et al., "Glycosaminoglycans In Normal and Osteoarthrotic Human Temporomandibular Joint Disks", Acta Odontologica Scandinavica, 50:112-119 (1992).
Bos et al., Structural and Mechanical Comparison of Human Ear, Alar, and Septal Cartilage, PRS Global Open, 2018, 9 pages.
Elliott et al. "Changes With Age In the Glycosaminoglycans of Human Articular Cartilage", Annals of the Rheumatic Diseases, 38:371-377 (1979).
Erten et al., "Detergent-Free Decellularization of Bovine Costal Cartilage for Chrondrogenic Differentiation of Human Adipose Mesenchymal Stem Cells in Vitro", RSC Advances, 6;94236-94246 (2016).
Herwig et al. "Chemical Changes of Human Knee Joint Menisci in Various Stages of Degeneration", Annals of the Rheumatic Diseases, 43:635-640 (1984).
Mankin et al., "Biochemical and Metabolic Abnormalities in Articular Cartilage from Osteo-Arthritic Human Hips", The Journal of Bone and Joint Surgery, 52-A(3): 424-434 (1970).
Maroudas et al., "Further Studies on the Composition of Human Femoral Head Cartilage", Annals of the Rheumatic Diseases, 39:514-523 (1980).
Muir et al., "The Distribution of Collagen in Human Articular Cartilage with Some of its Physiological Implications", The Journal of Bone and Joint Surgery, 52B(3):554-563 ((1970).
Rains et al., "Mechanical Properties of Human Tracheal Cartilage", Tracheal Cartilage Mechanics, pp. 219-225 (1992).
Zhou et al., "Cartilage Engineering Using Chondrocyte Cell Sheets and Its Applicaiton in Reconstruction of Microtia", Int. J. Clin Exp Pathol, 8(1):73-80, (2015).

* cited by examiner (A)

(B)

(C)

(D)

(E)

(A)

(B)

(C)

(D)

(E)

(A)

(B)

(C)

(A)

(B)

(A)

(B)

(C)

CARTILAGE MATRIX

CROSS-REFERENCE TO RELATED APPLICATIONS

This application is a U.S. National Phase application of International Application No. PCT/US2018/043144, filed Jul. 20, 2018 claiming the benefit of U.S. Provisional Application No. 62/535,151, entitled CARTILAGE MODIFICATIONS, filed Jul. 20, 2017, the contents of which are incorporated herein by reference in their entireties for all purposes.

FIELD OF THE INVENTION

The invention relates generally to a cartilage matrix and its preparation and uses.

BACKGROUND OF THE INVENTION

Cartilage (hyaline cartilage or articular cartilage) is a thin resilient and smooth elastic tissue covering bone surfaces inside joints. Cartilage is composed of chondrocytes that produce a large amount of collagenous extracellular matrix and ground substance rich in proteoglycan and elastin fibers. There are three types of cartilages: elastic cartilage, hyaline cartilage and fibrocartilage, differing in the relative amounts of collagen and proteoglycan. Cartilage damage usually starts with a local "pothole" in the cartilage, and then enlarges over time until all cartilage is worn away. While cartilage damage can be treated with cartilage repair, cartilage has limited repair capabilities because chondrocytes are bound in lacunae and cannot migrate to damaged areas. Thus, cartilage damage is difficult to heal. Various procedures have been developed to heal cartilage damage by filing the cartilage defect with a repair tissue. There remains a need for cartilage repair tissues that are cohesive, tacky and malleable.

SUMMARY OF THE INVENTION

The present invention relates to a cartilage matrix having a high decellularization level and a low glycosaminoglycan (GAG) content.

A cartilage matrix is provided. The cartilage matrix has a decellularization level of greater than 90% and a glycosaminoglycan (GAG) content of no more than 20 wt % based on the dry weight of the cartilage matrix. The cartilage matrix may be prepared from a cartilage selected from the group consisting of an articular cartilage, a costal cartilage, an auricular cartilage, and a nasal cartilage. The cartilage matrix may be in the form of a putty, a gel, a sheet, a disc, a tape, a sponge, a cube, a solid cylinder, a hollow cylinder, powder or particles, preferably in the form of a putty.

The cartilage matrix may be cohesive. The cartilage matrix may be tacky. The cartilage matrix may be malleable. The cartilage matrix may have a particle size of less than 250 μm. The cartilage matrix may have a residual calcium content of less than 50 wt % based on the dry weight of the cartilage matrix. The cartilage matrix may have a devitalization level of greater than 90%. The cartilage matrix may be dehydrated. The cartilage matrix may be freeze-dried. The cartilage matrix may be lyophilized. The cartilage matrix may be sterilized. The cartilage matrix may be frozen. The cartilage matrix may be cryopreserved.

A composition comprising the cartilage matrix of the present invention is also provided. The composition may further comprise cartilage particulates. The cartilage particulates may have not been treated by an enzyme selected from the group consisting of a glycolytic enzyme, a proteolytic enzyme and a combination thereof. The composition may comprise the cartilage matrix and the cartilage particulates at a weight ratio from 20:1 to 1:20.

The composition may further comprise tissue fragments having viable cells. The tissue fragments may be cryopreserved. The tissue fragments may be obtained from a donor who is a recipient of the cartilage matrix. The tissue fragments may be obtained from a donor who is not a recipient of the cartilage matrix. The tissue fragments may be obtained from a cartilage. The tissue fragments may be obtained from a placenta. The composition may comprise the cartilage matrix and the tissue fragments at a weight ratio from 20:1 to 1:20.

The composition may further comprise demineralized bone matrix (DBM) particles. The composition may comprise the cartilage matrix and the DBM particulates at a weight ratio from 50:1 to 1:50. The DBM particulates may be distributed in the cartilage matrix at a DBM density going up from one side of the cartilage matrix to another side of the cartilage matrix.

The composition may further comprise non-demineralized bone particulates.

The composition may further comprise cortical bone, cancellous bone, and/or cortical cancellous bone, which may be in form of fibers, chips or particles.

The composition may further comprise saline, water, whole blood, blood plasma or whole blood-derived, noncellular components.

The composition may further comprise a bioactive agent. The bioactive agent may be an antibiotic. The bioactive agent may be a growth factor.

The composition may further comprise viable cells selected from the group consisting of chondrocytes, chondroblasts, progenitor cells, stem cells and combinations thereof.

The viable cells may be cryopreserved. The viable cells may be seeded to a collagen matrix prior to surgery. The viable cells may be obtained from a donor who is a recipient of the cartilage matrix. The viable cells may be obtained from a donor who is not a recipient of the cartilage matrix. The viable cells may be obtained from a juvenile donor. The viable cells may be obtained from an adult donor. The viable cells may be chondrocytes. The chondrocytes may be cultured.

The composition may further comprise a fresh cartilage. The fresh cartilage may be not decellularized and not deglycosylated. The fresh cartilage may be prepared from a cartilage selected from the group consisting of an articular cartilage, a costal cartilage, an auricular cartilage, and a nasal cartilage. The fresh cartilage may be present at no more than 90 wt % based on the total weight of the composition.

An implant comprising the composition of the present invention is provided. The implant may further comprise a synthetic material. The synthetic material may comprise a non-degradable material (e.g., polyethylene, polypropylene, polymethyl methacrylate, polyurethane, polyether ether ketone (PEEK) and polydimethylsiloxane (PDMS)), a (bio) degradable polymer (e.g., polyglycolic acid, polylactic acid and copolymers), or a combination thereof. The synthetic material may comprise an inorganic material such as tricalcium phosphate, apatites, hydroxyapatites, or a non-crystalline amorphous, silica-based material (e.g., bioglass). The synthetic material may be selected from the group consisting of ceramics, hydroxyapatite, calcium phosphate, calcium sulfate, calcium carbonate, hyaluronic acid, proteoglycans, laminin, fibronectin, polyethylene glycol, polymethylmethacrylate, polyurethane, acryloylmorpholine, N,N-dimethyl acrylamide, N-vinyl pyrrolidone and tetrahydrofurfuryl methacrylate, polyurethane, polylactic acid and a combination thereof.

A package comprising the cartilage matrix of the present invention is provided. A package comprising the cartilage matrix of the present invention and a liquid for reconstitution of the cartilage matrix. The liquid may comprise saline, water, whole blood, blood plasma or whole blood-derived, non-cellular components. The liquid may comprise a bioactive agent. The bioactive agent may an antibiotic. The bioactive agent may be a growth factor. In the package, the cartilage matrix may be packed as a sheet, powder or ready-to-use putty. The package may be a jar, pouch, tray or syringe.

A method of making an implant is provided. The method comprises molding the cartilage matrix of the present invention into a molded cartilage matrix having a predetermined shape, and the molded cartilage matrix may remain in the predetermined shape for at least 30 minutes. The method may further comprise adding a liquid to the cartilage matrix. The liquid may comprise saline, water, whole blood, blood plasma or whole blood-derived, non-cellular components. The liquid may comprise a bioactive agent. The bioactive agent may be an antibiotic. The bioactive agent may be a growth factor.

A method of treating a tissue or organ defect in a subject is provided. The method comprises applying to the tissue or organ defect an effective amount of the cartilage matrix of the present invention.

A method of treating a tissue or organ defect in a subject is provided. The method comprises applying to the tissue or organ defect an effective amount of the composition of the present invention.

A method of treating a tissue or organ defect in a subject is provided. The method comprises placing the implant of the present invention at the tissue or organ defect.

A method of preparing a cartilage matrix is provided. The method comprises decellularizing a cartilage to generate a decellularized cartilage, and deglycosylating the decellularized cartilage. The cartilage may be selected from the group consisting of an articular cartilage, a costal cartilage, an auricular cartilage, and a nasal cartilage. The cartilage matrix may be in the form of a putty, a gel, a sheet, a disc, a tape, a sponge, a cube, a solid or hollow cylinder, powder or particles. The cartilage matrix may be in the form of a putty.

The cartilage matrix prepared according to the present invention may exhibit cohesiveness about 5-90% greater than that of an untreated cartilage. The cartilage matrix prepared according to the present invention may exhibit adhesiveness about 0.5-90 times greater than that of an untreated cartilage.

The decellularization step may comprise treating the cartilage with a detergent. The deglycosylation step may comprise treating the decellularized cartilage with a detergent.

The cartilage matrix preparation method may further comprise demineralizing the decellularized cartilage. The cartilage matrix preparation method may further comprise demineralizing the cartilage matrix. The deglycosylation step may comprise incubating the decellularized cartilage in a solution comprising a glycolytic enzyme, a proteolytic enzyme, a chemical compound, physical treatment (e.g., heat treatment with or without partial tissue gelatinization) or a combination thereof. The glycolytic enzyme may be selected from the group consisting of a deglycosidase, an endoglycosidase, a hyaluronidase and a chondroitinase. The deglycosidase may be selected from the group consisting of PNGase F, O-glycosidase, neuraminidase, $\beta$ 1-4 galactosidase and $\beta$-N-acetylglucosaminidase. The proteolytic enzyme may be selected from the group consisting of pepsin, papain, proteinase, trypsin, collagenase, dispase, chymotrypsin, and a proenzyme thereof. The proteolytic enzyme may be pepsin or papain. The chemical compound may be selected from the group consisting of trichloroacetic acid trifluoromethanesulfonic acid, hydrazine and a combination thereof. The deglycosylation step may comprise incubating the decellularized cartilage in an acidic solution having a pH lower than 2. The cartilage may be incubated in the acidic solution for about 0.01, 0.1, 1, 12, 24, 48 or 72 hours, or about 1-180, 1-120, 1-60 or 1-30 minute(s).

The cartilage matrix preparation method may further comprise adding an effective amount of a buffer to the acidic solution to adjust pH of the resulting solution after the incubation. The adjusted pH is 2.5-7.

The cartilage matrix preparation method may further comprise storing the cartilage matrix in a storage solution. The storage solution may be glycerol, a buffer, or a cryopreservation solution.

The cartilage matrix preparation method may further comprise drying the cartilage matrix. The decellularized cartilage may be milled before the deglycosylation step. The cartilage matrix preparation method may further comprise devitalizing the cartilage matrix.

A cartilage matrix prepared according to the method of the present invention is provided.

DETAILED DESCRIPTION OF THE INVENTION

Figure 1:
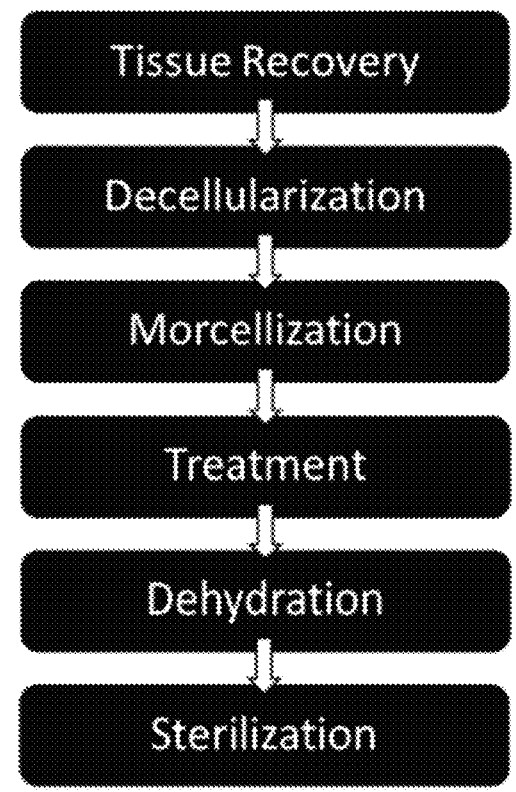
FIG. 1 illustrates (A) preparation of articular demineralized cartilage matrix with (B) a deglycosylase treatment and an optional additional particle demineralization.
Figure 1:
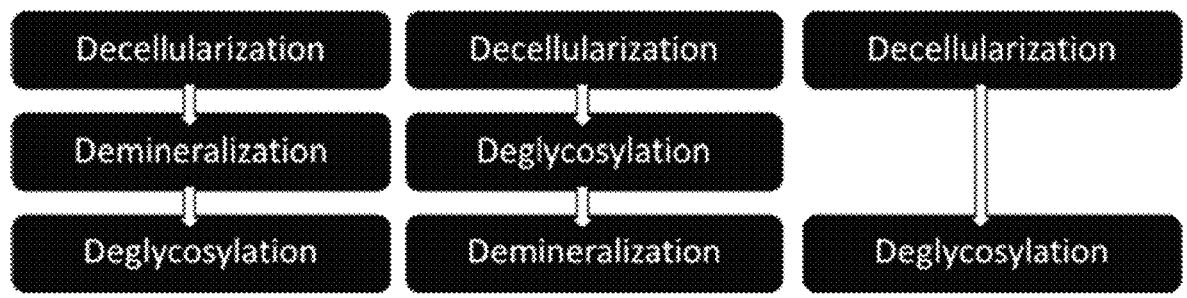
Figure 2:
FIG. 2 shows (A) grated pieces of articular cartilage after cartilage isolation, (B) pieces of costal cartilage after cartilage isolation, (C) mineralized cartilage matrix particles following morcelization, (D) macroscopic appearance of demineralized cartilage matrix following pepsin treatment and dehydration, and (E) microscopic appearance of demineralized cartilage matrix following pepsin treatment and dehydration showing the presence of particles and solubilate.
Figure 2:
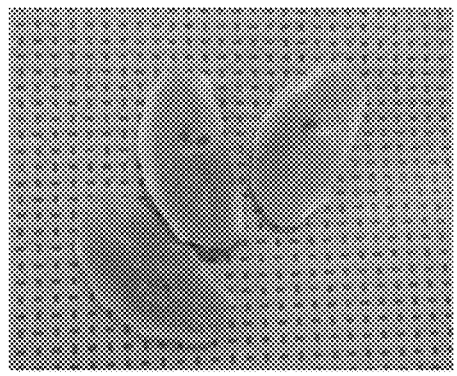
Figure 2:
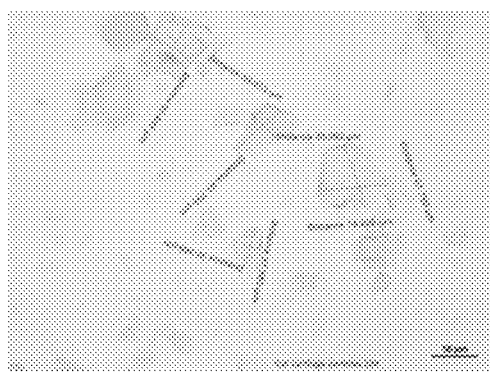
Figure 2:
Figure 2:
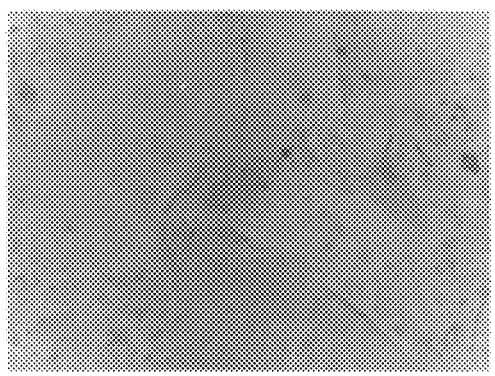

The present invention relates to a cartilage matrix having a high decellularization level and a low glycosaminoglycan (GAG) content and its preparation and uses. The inventors have discovered that such a cartilage matrix exhibits surprisingly desirable characteristics, for example, cohesiveness, tackiness and malleability, for use in cartilage repair.

Unless stated otherwise, a wt % figure for an ingredient of a composition is relative to the total weight of the composition.

The term "cartilage" as used herein refers to a connective tissue that may cover and protect the ends of bones at the joints. The cartilage may be selected from the group consisting of articular cartilage, costal cartilage, auricular cartilage, nasal cartilage, and a combination thereof. The cartilage may be natural cartilage, synthetic cartilage, modified cartilage or a combination thereof. The cartilage may have one or more modifications. The modifications include decellularization, deglycosylation, demineralization, morcellization, dehydration, sterilization or a combination thereof. The modifications may be carried out simultaneously or sequentially. The modifications may be throughout the entire cartilage structure or on the surface of the cartilage, for example, within 10 μm, 20 μm, 30 μm, 50 μm, 100 μm, 300 μm, 1 mm, 2 mm, 3 mm or 10 mm from the surface of the cartilage.

The present invention provides a cartilage matrix having a high decellularization level and a low glycosaminoglycan (GAG) content. The term "cartilage matrix" as used herein refers to a modified cartilage tissue after one or more modifications such as decellularization, deglycosylation, demineralization, morcellization, dehydration, sterilization or a combination thereof. For example, the cartilage matrix may be a cartilage tissue after being subject to decellularization, deglycosylation, and optional demineralization. The cartilage matrix may consist of collagen and other extracellular matrices (ECM).

The term "decellularization" as used herein refers to a process, during which cells are removed from a cartilage tissue. The term "decellularization level" as used herein refers to the percentage of cells removed from a cartilage matrix. A cartilage matrix may have a decellularization level of greater than about 10, 20, 30, 40, 50, 60, 70, 75, 80, 90, 91, 92, 93, 94, 95, 96, 97, 98, 99 or 99.9%. In one embodiment, the cartilage matrix has a decellularization level greater than about 90%. A high decellularization level is a desirable for the cartilage matrix to avoid a potential immunogenic reaction by a subject to whom the cartilage matrix is applied to treat a disease or condition, for example, a tissue or organ defect.

Glycosaminoglycans (GAGs) are long unbranched polysaccharides consisting of a repeating disaccharide unit. Based on core disaccharide structures, GAGs are classified into four groups, including hyaluronic acid, keratan sulfate, and chondroitin sulfate. Glycosaminoglycans are highly polar and attract water acting as tissue lubricant or—especially as in the case of cartilage—as a shock absorber. The cartilage matrix may have a GAG content of no more than about 40, 30, 20, 10 or 5 wt %, for example, no more than about 20 wt %, based on the dry weight of the cartilage matrix. The selective reduction in a tissue's GAG content will change its charge characteristics and water content. These changes will directly alter the tissue's biomechanical profile and, in the case of cartilage particles, are assumed to allow the collagenous extracellular matrix of discrete particles to interact directly with one another resulting in the formation of a cohesive, tacky and malleable cartilage putty.

The cartilage matrix may be prepared from a cartilage. The cartilage may be selected from the group consisting of an articular cartilage, a costal cartilage, an auricular cartilage, a nasal cartilage and a combination thereof.

The cartilage matrix may be in any form. For example, the cartilage matrix may be in the form of a putty, a gel, a sheet, a disc, a tape, a sponge, a cube, a solid cylinder, a hollow cylinder, powder or particles. In one embodiment, the cartilage matrix is in the form of a putty.

The cartilage matrix may be cohesive. The cartilage matrix may be cohesive after being wetted with a liquid and molded, by hand or otherwise, into a desirable mass or shape. The term "cohesive" or "cohesiveness" as used herein refers to the capability of the cartilage matrix to retain at least a predetermined portion of an initial mass (e.g., at least about 10, 20, 30, 40, 50, 60, 70, 80, 90 or 95% by weight) or shape (e.g., volume) (e.g., at least about 10, 20, 30, 40, 50, 60, 70, 80, 90 or 95% by volume) for a predetermined period of time in a predetermined environment. The molded mass may be picked up and handled without losing a substantial portion (e.g., losing at least about 10, 20, 30, 40, 50, 60, 70, 80, 90 or 95 wt %) of its mass. The predetermined period of time may be about 1, 5, 10, 30, 45 seconds, 1, 5, 10, 30, 60, 120, 180, 240 or 480 minutes, for example, about 10, 60 or 180 minutes. The predetermined environment may be a liquid environment. For example, the cartilage matrix may be in contact with or submerged by a liquid. The weight ratio between the cartilage matrix and the liquid may be in the range between about 1:0.5 and 1:1,000, for example, between about 1:1 to 1:100. The volume ratio between the cartilage matrix and the liquid may be in the range between about 1:0.5 and 1:1,000, for example, between about 1:1 and 1:100. The liquid may be a buffer (e.g., saline), blood, or a combination thereof. The aqueous solution may be still or flowing at a speed of, for example, about 5-500 rpm or 1-60,000 mm per minute.

The cohesiveness of the cartilage matrix may be determined by measuring biomechanical properties such as elasticity, plasticity via strain/deformation, and/or compression, tensile, shear stress testing, or volume expansion after hydration.

The cartilage matrix may be cohesive in the absence of a binder or a cross-linking agent. Examples of binders include glycerol (e.g., PRESERVON®), acidic solutions (e.g., lactic and trifluoroacetic acid), buffering solutions (e.g., phosphate), and adhesive binders (e.g., gelatin, fibrin glues, bone cements or liquefied bone). The cross-linking agent may be selected from the group consisting of 1-Ethyl-3-(3-dimethylaminopropyl) carbodiimide (EDC), EDC/hyaluronic acid, genipin, hyaluronic acid and glutaraldehyde. The cartilage matrix may be cohesive with a binder as above. In one embodiment, the cartilage matrix may be combined and stored with glycerol. In another embodiment, the cartilage matrix may be combined and stored with hyaluronic acid.

The cartilage matrix may be cohesive when a small amount of pressure is applied to the cartilage matrix. The small amount of pressure may range from about 1 Pa to about 100 Pa, from about 100 Pa to about 1,000 Pa, from about 1 kPa to about 10 kPa, form about 10 KPa to about 50 kPa, from about 50 kPa to about 100 kPa or from about 100 kPa to 1 MPa. The pressure may be applied to the cartilage matrix by mechanical force, with or without a device.

The cartilage matrix may have a predetermined specific surface area. The term "specific surface area" used herein refers to the total surface area of the cartilage matrix per unit of mass or volume of the cartilage matrix. The specific surface area of the cartilage matrix may be measured by conventional techniques known in the art. The specific surface area may be measured in an adsorption based method, in which the cartilage matrix may be exposed to an absorbate molecule (i.e., a probe molecule) under a predetermined condition for a predetermined period of time before quantifying the amount of the probe molecule absorbed to the cartilage matrix.

The specific surface area of the cartilage matrix may be determined by protein adsorption or gas sorption method. The specific surface area of the) may be at least about 20, 50, 100, 150, 200, 250, 500, 750 or 1,000 $cm^2/g$ or at least about 10, 37, 50, 100, 150, 200, 250, 500, 750 or 1,000 $cm^2/cm^3$. The specific surface area of the cartilage matrix may be in the range of about 20-20,000 $cm^2/g$, 20-100 $cm^2/g$, 20-200 $cm^2/g$, 100-200 $cm^2/g$, 100-300 $cm^2/g$, 100-400 $cm^2/g$, 100-500 $cm^2/g$, 100-600 $cm^2/g$, 200-500 $cm^2/g$, 300-500 $cm^2/g$, 300-1000 $cm^2/g$, 500-1,000 $cm^2/g$, 1,000-3,000 $cm^2/g$, 3,000-10,000 $cm^2/g$, 10,000-20,000 $cm^2/g$, 50-100 $cm^2/g$, 50-200 $cm^2/g$, 50-300 $cm^2/g$, 75-300 $cm^2/g$, 200-400 $cm^2/g$ or 300-1,000 $cm^2/g$. The specific surface area of the cartilage matrix may be in the range of about 1-5 $cm^2/cm^3$, 1-10 $cm^2/cm^3$, 5-10 $cm^2/cm^3$, 10-20 $cm^2/cm^3$, 10-30 $cm^2/cm^3$, 10-40 $cm^2/cm^3$, 10-50 $cm^2/cm^3$, 10-60 $cm^2/cm^3$, 10-100 $cm^2/cm^3$, 50-150 $cm^2/cm^3$, 75-125 $cm^2/cm^3$, 37-37,000 $cm^2/cm^3$, 37-185 $cm^2/cm^3$, 37-370 $cm^2/cm^3$, 185-925 $cm^2/cm^3$, 370-925 $cm^2/cm^3$, 555-925 $cm^2/cm^3$, 925-1,850 $cm^2/cm^3$, 1,850-5,550 $cm^2/cm^3$, 5,550-18,500 $cm^2/cm^3$, 18,500-37,000 $cm^2/cm^3$, 92.5-185 $cm^2/cm^3$, 139-555 $cm^2/cm^3$, 370-740 $cm^2/cm^3$ or 555-1,850 $cm^2/cm^3$.

The cartilage matrix may be tacky. The term "tacky" or "tackiness" as used herein refers to the capability of the cartilage matrix to adhere to another material.

The cartilage matrix may be malleable. The term "malleable" or "malleability" as used herein refers to the capability of the cartilage matrix to be shaped into a desirable form by applying a force, for example, pressure.

The cartilage matrix may be highly moldable with a low elasticity. The terms "moldable" or "moldability" used herein refer to the capability of the cartilage matrix to be deformed, i.e., to change its size and/or shape. The terms "elasticity" and "elastic" used herein refer to the capability of the cartilage matrix to recover its size and/or shape after being molded or deformed (e.g., being stretched or compressed). The cartilage matrix may have an elastic modulus (also known as modulus of elasticity, tensile modulus or Young's modulus) of less than about 500, 400, 300, 200, 150, 100, 50 or 10 kPa, or in a range of about 10-500, 10-200 or 50-100 kPa.

The cartilage matrix may have an average particle size in the range of about 5-5,000 µm, 5-10 µm, 5-25 µm, 5-50 µm, 5-75 µm, 5-100 µm, 5-200 µm, 10-25 µm, 10-50 µm, 10-75 µm, 10-100 µm, 10-200 µm, 10-300 µm, 10-450 µm, 25-50 µm, 25-75 µm, 25-100 µm, 25-150 µm, 25-200 µm, 25-300 µm, 25-450 µm, 50-75 µm, 50-100 µm, 50-250 µm, 50-300 µm, 50-450 µm, 50-1,000 µm, 100-500 µm or 150-250 µm, or less than about 5,000 µm, 1,000 µm, 500 µm, 250 µm, 100 µm or 50 µm. For example, the cartilage matrix may have a particle size of less than 250 µm. In one embodiment, the cartilage matrix may have a particle size distribution, in which about 25-35% of the particles have a particle size less than about 50 µm, about 45-55% of the particles have a particle size in the range of about 50-100 µm, and/or about 15-25% of the particles have a particle size in the range of about 100-150 µm.

The cartilage matrix may not comprise fibers in a significant amount, for example, greater than about 5, 10, 20, 30, 40, 50, 60, 70, 80 or 90 wt %, based on the dry weight of the cartilage matrix. The term "fiber" used herein refers to a material whose longest dimension is at least 5, 10, 50 or 100 times of its shortest dimension or whose shortest dimension is greater than 250, 300, 400 or 500 µm.

The cartilage matrix may be demineralized. The term "demineralization" as used herein refers to a process during which inorganic minerals (e.g., hydroxyapatite) are removed from a cartilage tissue leaving a cartilage matrix consisting mainly of collagen and other extracellular matrices (ECM). After demineralization, calcium is released from the cartilage matrix. The extent of demineralization may be characterized based on the content (wt %) of the residual calcium in the cartilage matrix, for example, based on the dry weight of the cartilage matrix.

The cartilage matrix of the present invention may have a residual calcium content of less than about 50 wt % (e.g., about 50 wt %, 40 wt %, 30 wt %, 20 wt %, 10 wt %, 9 wt %, 8 wt %, 7 wt %, 6 wt %, 5 wt %, 4 wt %, 3 wt %, 2 wt %, 1 wt %, 0.5 wt %, 0.1 wt % or 0.01 wt %), less than about 6 wt % (e.g., in the range of about 0.001-6 wt %, 0.1-6 wt %, 0.5-1 wt %, 0.5-2 wt %, 0.5-3 wt %, 0.5-4 wt %, 0.5-5 wt %, 0.5-6 wt %, 0.5-7 wt %, 0.5-8 wt %, 1-6 wt %, 2-6 wt %, 2-5 wt %, 0.01-0.5 wt %, 0.5-1 wt %, 1-2 wt %, 2-3 wt %, 3-4 wt %, 4-5 wt % or 5-6 wt %), less than about 4 wt % (e.g., about 0.5-3 wt %), based on the dry weight of the demineralized cartilage matrix. For example, the cartilage matrix may have a residual calcium content of less than about 6 wt % (e.g., about 0.3-3.5 wt %), based on the dry weight of the cartilage matrix. The demineralization may be throughout the entire structure or on the surface of the cartilage matrix, for example, within 10 µm, 20 µm, 30 µm, 50 µm, 100 µm, 300 µm, 1 mm, 2 mm, 3 mm or 10 mm from the surface of the cartilage matrix.

The cartilage matrix may be devitalized. The term "devitalization" as used herein refers to a process in which viable cells are killed. The term "devitalization level" used herein refers to the percentage of viable cells killed in a cartilage matrix by devitalization. The cartilage matrix may have a devitalization level of greater than about 10%, 20%, 30%, 40%, 50%, 60%, 70%, 75%, 80%, 90%, 91%, 92%, 93%, 94%, 95%, 96%, 97%, 98%, 99% or 99.9%. In one embodiment, the cartilage matrix may have a devitalization level of greater than about 90%. The devitalization level may be evidenced by reduction of DNA content in a cartilage matrix after devitalization. For example, the cartilage matrix may have reduction of DNA content by at least about 10%, 20%, 30%, 40%, 50%, 60%, 70%, 75%, 80%, 90%, 91%, 92%, 93%, 94%, 95%, 96%, 97%, 98%, 99% or 99.9% after devitalization.

The cartilage matrix may be dehydrated. The cartilage matrix may be preserved in a hydrated state, for example, an aqueous medium or an organic or inorganic storage solution.

The cartilage matrix may be freeze-dried or lyophilized. The cartilage matrix may be sterilized, frozen or cryopreserved.

A composition comprising the cartilage matrix of the present invention is also provided. The composition may further comprise cartilage particulates. The cartilage particulates may have not been treated by an enzyme. The enzyme may be selected from the group consisting of a glycolytic enzyme, a proteolytic enzyme and a combination thereof. The composition may comprise the cartilage matrix and the cartilage particulates at a weight ratio from about 20:1 to about 1:20, from about 10:1 to about 1:10, from about 20:1 to about 1:1 or from about 1:1 to about 1:20, for example, 20:1, 15:1, 10:1, 9:1, 8:1, 7:1 . . . 1:1, 1:2, 1:3, 1:10, 1:15, 1:20.

The composition may further comprise tissue fragments having viable cells. The tissue fragments may be cryopreserved. The tissue fragments may be obtained from a donor who is a recipient of the cartilage matrix or a donor who is not a recipient of the cartilage matrix. The tissue fragments may be obtained from a cartilage. The tissue fragments may be obtained from a placenta. The composition may comprise the cartilage matrix and the tissue fragments at a weight ratio from about 20:1 to about 1:20, from about 10:1 to about 1:10, from about 20:1 to about 1:1 or from about 1:1 to about 1:20, for example, 20:1, 15:1, 10:1, 9:1, 8:1, 7:1, 6:1, 5:1, 4:1, 3:1, 2:1, 1:1, 1:2, 1:3, 1:10, 1:15, 1:20.

The composition may further comprise demineralized bone matrix (DBM) particles. The composition may comprise the cartilage matrix and the DBM particulates at a weight ratio from about 50:1 to about 1:50, from about 50:1 to about 1:1, from about 1:1 to about 1:50, from about 25:1 to about 1:25, from about 25:1 to about 1:1, from about 1:1 to about 1:25, for example, about 50:1, 40:1, 30:1, 20:1, 15:1, 10:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:30, 1:40, 1:50. The DBM particulates may be distributed in the cartilage matrix randomly, evenly or at a DBM density gradient in a desirable direction within the cartilage matrix, for example, going up from one side of the cartilage matrix to another side of the cartilage matrix.

The composition may further comprise non-demineralized bone particulates. The composition may comprise the cartilage matrix and the non-demineralized bone particulates at a weight ratio from about 50:1 to about 1:50, from about 50:1 to about 1:1, from about 1:1 to about 1:50, from about 25:1 to about 1:25, from about 25:1 to about 1:1, from about 1:1 to about 1:25, for example, about 50:1, 40:1, 30:1, 20:1, 15:1, 10:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:30, 1:40, 1:50. The DBM particulates may be distributed in the cartilage matrix randomly, evenly or at a non-demineralized bone density going up from one side of the cartilage matrix to another side of the cartilage matrix.

The composition may further comprise cortical bone, cancellous bone, and/or cortical cancellous bone, which may be in form of fibers, chips or particles.

The composition may further comprise saline, water, whole blood, blood plasma or whole blood-derived, non-cellular components. The term "whole blood-derived, non-cellular components" used herein refers to cell fragments (e.g. platelet-rich plasma (PRP)) and cryoprecipitants containing bioactive factors, including fibrinogen, coagulation factors, and immunoglobulins.

The composition may further comprise a pharmaceutically acceptable carrier or diluent. Carriers, diluents and excipients suitable in the pharmaceutical composition are well known in the art.

The composition may further comprise a bioactive agent. The bioactive agent has a biological activity and may be a chemical compound, a biological molecule or a combination thereof. Examples of the bioactive agent include an antibiotic, a growth factor, collagen, a glycosaminoglycan, osteonectin, bone sialo protein, an osteoinductive factor, a chondrogenic factor, a cytokine, a mitogenic factor, a chemotactic factor, an angiogenic factor, a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), insulin and an interleukin. The growth factor may be an osteogenic growth factor, a transforming growth factor (TGF), a fibroblast growth factor (FGF), an insulin-like growth factor (IGF), a platelet-derived growth factor (PDGF), an epidermal growth factor (EGF), a vascular endothelial growth factor (VEGF) or a nerve growth factor (NGF). The BMP may be BMP-2, BMP-3, BMP-4, BMP-5, BMP-6, BMP-7, BMP-8, BMP-9, BMP-10, BMP-11, BMP-12, BMP-13, BMP-14, BMP-15, any truncated or modified forms of BMP-2, BMP-3, BMP-4, BMP-5, BMP-6, BMP-7, BMP-8, BMP-9, BMP-10, BMP-11, BMP-12, BMP-13, BMP-14 or BMP-15.

The composition may further comprise viable cells. The viable cells may be selected from the group consisting of chondrocytes, chondroblasts, progenitor cells, stem cells and combinations thereof. The viable cells may be chondrocytes. The chondrocytes may be cultured. Examples of the stem cells include embryonic stem cells, tissue-specific stem cells such as bone marrow or adipose tissue-derived stem cells, and induced stem cells such as induced pluripotent stem cells (IPSCs). The viable cells may be cryopreserved. The viable cells may be seeded to a collagen matrix prior to surgery. The viable cells may be obtained from a donor who is a recipient of the cartilage matrix or a donor who is not a recipient of the cartilage matrix. The viable cells may be obtained from a juvenile donor or an adult donor. The viable cells may be obtained from bone such as cortical bone, cancellous bone, and/or cortical cancellous bone.

The composition may further comprise a fresh cartilage. The term "fresh cartilage" used herein refers to a cartilage tissue obtained from a donor without being frozen and having viable cells from the donor. The fresh cartilage may be selected from the group consisting of articular cartilage, costal cartilage, auricular cartilage, nasal cartilage, and a combination thereof. In one embodiment, the fresh cartilage may be not decellularized and not deglycosylated. The fresh cartilage may be present at no more than about 95, 90, 85, 80, 70, 60, 50, 40, 30, 20 or 10 wt % based on the total weight of the composition.

The fresh cartilage may comprise viable cells. The viable cells may be selected from the group consisting of chondrocytes, chondroblasts, progenitor cells, stem cells and combinations thereof. Examples of the stem cells include embryonic stem cells, tissue-specific stem cells such as bone marrow or adipose tissue-derived stem cells, and induced stem cells such as induced pluripotent stem cells (IPSCs). The volume ratio between the fresh cartilage and the cartilage matrix may be in the range from about 1:1 to about 4:1, from about 1.5:1 to about 3:1, from about 1:1 to about 3:1, or from about 1.5:1 to about 2.5:1, for example, about 2:1.

For each cartilage matrix of the present invention, an implant comprising the cartilage matrix is provided. The term "implant" as used herein refers to an object designed to be placed partially or wholly within the body of a subject for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. The subject may be a living animal in need of a bone implant, preferably a mammal. The mammal may be a human, a cow, a pig, a dog, a cat, a non-human primate, a rodent such as a rat or mouse, a horse, a goat, a sheep, or a deer. The implant may further comprise a synthetic material.

For each implant of the present invention, a method of making the implant is provided. The method comprises molding the cartilage matrix into a predetermined shape for at least a predetermined period of time, which may be about 1, 5, 10, 30, 45 seconds, 1, 5, 10, 30, 60, 120, 180, 240 or 480 minutes, for example, about 10, 30, 60 or 180 minutes. The method may further comprise adding a liquid to the cartilage matrix. The liquid may comprise saline, water, whole blood, blood plasma or whole blood-derived, non-cellular components. The liquid may comprise a bioactive agent such as an antibiotic or a growth factor.

For each cartilage matrix of the present invention, a package comprising the cartilage matrix of the present invention is provided. A package comprising the cartilage matrix of the present invention and a liquid for reconstitution of the cartilage matrix. The liquid may comprise saline, water, whole blood, blood plasma or whole blood-derived, non-cellular components. The liquid may comprise a bioactive agent. The bioactive agent may an antibiotic. The bioactive agent may be a growth factor. In the package, the cartilage matrix may be packed as a sheet, powder or ready-to-use putty. The package may be a jar, pouch, tray or syringe.

The package may further comprise viable cells, a fresh cartilage or a combination thereof. The viable cells may be selected from the group consisting of chondrocytes, chondroblasts, progenitor cells, stem cells and combinations thereof. Examples of the stem cells include embryonic stem cells, tissue-specific stem cells such as bone marrow or adipose tissue-derived stem cells, and induced stem cells such as induced pluripotent stem cells (IPSCs). The fresh cartilage may be selected from the group consisting of articular cartilage, costal cartilage, auricular cartilage, nasal cartilage, and a combination thereof. In one embodiment, the fresh cartilage may be not decellularized and not deglycosylated. When both in the package, the fresh cartilage and the viable cells may be placed in the same or different compartments of the package such as pouches.

The package may further comprise a liquid for reconstitution of the cartilage matrix in the package. The liquid may comprise saline, water, whole blood, blood plasma or whole blood-derived, non-cellular components. The liquid may comprise antibiotics, a bioactive factor, a growth factor or a combination thereof.

Various uses of the cartilage matrix of the present invention are provided.

The term "an effective amount" refers to an amount of a composition comprising the cartilage matrix required to achieve a stated goal (e.g., treating a tissue or organ defect in a subject). The effective amount of the composition comprising the cartilage matrix may vary depending upon the stated goals, the physical characteristics of the subject, the nature and severity of the defect, the existence of related or unrelated medical conditions, the nature of the cartilage matrix, the composition comprising the cartilage matrix, the means of administering the composition to the subject, and the administration route. A specific dose for a given subject may generally be set by the judgment of a physician. The composition may be administered to the subject in one or multiple doses. Each dose may be 0.1 cc, 0.2 cc, 0.5 cc, 1 cc, 2 cc, 5 cc, 10 cc, 20 cc, 30 cc, 50 cc, 100 cc, 200 cc, depends on the implantation site and surgery needs.

A method of treating a tissue or organ defect in a subject is provided. The method comprises applying to the tissue or organ defect an effective amount of the cartilage matrix of the present invention. In one embodiment, the method further comprises sealing the cartilage matrix applied to the tissue or organ defect. In another embodiment, the cartilage matrix does not need to be sealed by a sealant (e.g., a fibrin glue) after being applied to the tissue or organ defect.

A method of treating a tissue or organ defect in a subject is provided. The method comprises applying to the tissue or organ defect an effective amount of the composition of the present invention. In one embodiment, the method further comprises sealing the composition applied to the tissue or organ defect. In another embodiment, the composition does not need to be sealed by a sealant (e.g., a fibrin glue) after being applied to the tissue or organ defect.

A method of treating a tissue or organ defect in a subject, comprising placing the implant of the present invention. In one embodiment, the method further comprises sealing the implant applied to the tissue or organ defect. In another embodiment, the implant does not need to be sealed by a sealant (e.g., a fibrin glue) after being applied to the tissue or organ defect.

The effectiveness of the treatment of a tissue or organ defect in a subject may be determined based on formation of structural cartilage matrix and improvement of clinical symptoms.

The cartilage matrix may be used as a building material to cast simple structures or assemble complex 3D objects. Following manufacturing, the object may further be subjected to a secondary "curing/hardening" process through external means (e.g., chemical crosslinking) or the inclusion of a synthetic binder (e.g., polymer particles). The construct may be stored wet, for example, in an aqueous storage solution such as PRESERVON® or frozen prior to use. The final construct may contain cells, be stored in a nutrient-rich medium or be cryopreserved prior to use. This process may extend the use of the cartilage matrix, especially in applications where the structure, geometry, or biomechanical properties of the final construct need to be controlled. This would further allow the preshaping of implants for patient-specific applications. For each cartilage matrix of the present invention, a method for preparing the cartilage matrix is provided. The method comprises decellularizing a cartilage to generate a decellularized cartilage, and deglycosylating the decellularized cartilage. The cartilage may be selected from the group consisting of an articular cartilage, a costal cartilage, an auricular cartilage, and a nasal cartilage. The cartilage matrix may be in the form of a putty, a gel, a sheet, a disc, a tape, a sponge, a cube, a solid or hollow cylinder, powder or particles. The cartilage matrix may be in the form of a putty. The preparation method may be carried out at a not above ambient temperature (i.e., 25° C.), for example, above about 37° C., 50° C., 90° C., or 100° C.

The decellularization step may comprise treating the cartilage with a detergent. The deglycosylation step may comprise treating the decellularized cartilage with a detergent. The detergent may be any detergent suitable for decellularizing or devitalizing a tissue, preferably a cartilage tissue, more preferably a human cartilage tissue. The detergent may be selected from the group consisting of non-ionic detergents, ionic detergents, zwitterionic detergents or combinations thereof. Exemplary detergents include Triton X-100, sodium dodecyl sulfate (SDS), sodium deoxycholate, 3-[(3-cholamidopropyl) dimethylammonio]-1-propanesulfonate (CHAPS), Sulfobetaine-10 and -16, N-lauroylsarcosinate, Tri(n-butyl)phosphate, a polyoxyethylene alcohol, a polyoxyethylene isoalcohol, a polyoxyethylene p-t-octyl phenol, a polyoxyethylene nonylphenol, a polyoxyethylene ester of a fatty acid, and a polyoxyethylene sorbitol ester.

The decellularization step may comprise treating the cartilage with a solution comprising a detergent (e.g., sodium dodecyl sulfate (SDS), CHAPS), endonuclease or a combination thereof. The decellularized cartilage may be milled before the deglycosylation step.

The deglycosylation step may comprise incubating the decellularized cartilage in a solution comprising a glycolytic enzyme, a proteolytic enzyme, a chemical compound or a combination thereof. The glycolytic enzyme may be selected from the group consisting of a deglycosidase, an endoglycosidase, a hyaluronidase and a chondroitinase. The deglycosidase may be selected from the group consisting of PNGase F, O-glycosidase, neuraminidase, β 1-4 galactosidase and β-N-cetylglucosaminidase. The proteolytic enzyme may be selected from the group consisting of pepsin, papain, proteinase, trypsin, collagenase, dispase, chymotrypsin, and a proenzyme thereof. The proteolytic enzyme may be pepsin or papain. The chemical compound may be selected from the group consisting of trichloroacetic acid trifluoromethanesulfonic acid, hydrazine and a combination thereof.

The cartilage matrix prepared according to the present invention may exhibit cohesiveness about 1-10%, 5-90%, 10-80%, 20-70% or 30-60% greater than that of an untreated cartilage. In one embodiment, the cartilage matrix exhibits cohesiveness about 5-90% greater than that of an untreated cartilage.

The cartilage matrix prepared according to the present invention may exhibit adhesiveness 0.5-90 times, 1-50 times, 1-25 times, or 5-40 times greater than that of an untreated cartilage. In one embodiment, the cartilage matrix exhibits adhesiveness about 0.5-90 times greater than that of an untreated cartilage.

The term "untreated cartilage" used herein refers to a cartilage that has not been subject to decellularization and deglycosylation. In some embodiments, the untreated cartilage may be obtained from the same donor and/or the same organ as the cartilage used to make the cartilage matrix according to the present invention.

The cartilage matrix preparation method may further comprise a demineralization step after the decellularization step. The demineralization step may be carried out before or after the deglycosylation step. In the deglycosylation step, the decellularized cartilage or the cartilage matrix may be incubated in an acidic solution having a pH lower than 2 for a predetermined period of time, for example, about 0.01, 0.1, 1, 12, 24, 48 or 72 hours, or about 1-180, 1-120, 1-60 or 1-30 minute(s). The incubation step may be repeated for one, two or more additional times. The acid solution may comprise one or more enzymes. Examples of the enzymes include pepsin, proteinase, trypsin, collagenase, dispase, chymotrypsin, and their proenzymes. For example, the acid solution may comprise pepsin. The acid solution may have an enzyme concentration of about 0.001-100 mg/ml, for example, 0.01 mg/ml, 0.1 mg/ml, 0.5 mg/ml, 1 mg/ml, and 2 mg/ml.

After the incubation, an effective amount of a buffer may be added to the acidic solution to adjust pH of the resulting solution within a short period of time, for example, within about 300, 250, 200, 180, 150, 120, 90, 80, 60, 40, 30, 20, 10 or 5 seconds, or within about 5-300, 10-200 or 50-100 seconds. The resulting solution may have a pH of about 2.5-7, 3-7, 4-7, 4.5-7, 2.5-6.5, 3-6.5, 4-6.5, 5-6.5, 2.5-5, 3-5, 4-5, 2.5-4 or 3-4. The buffer may be a sodium glycinate buffer, a citrate buffer, a phosphate buffer, a carbonate buffer, a TRIS buffer or an acetate buffer having a concentration at, for example, about 10 M, 9 M, 8 M, 7 M, 6 M, 5 M, 4 M, 3 M, 2 M, 1 M or 0.5 M. A tissue culture medium, for example, Dulbecco's Modified Eagle Medium (DMEM), RPMI, or (Minimum Essential Media) MEM, may be added after the acid/buffer solution is removed. The demineralized cartilage or the demineralized cartilage matrix may be rinsed with saline.

The preparation method may further comprise storing the cartilage matrix in a storage solution. The storage solution may be glycerol, a buffer or a cryopreservation solution. The cartilage matrix may be stored at room temperature. During storage, the cartilage matrix may retain a significant level of, for example, at least about 50%, 60%, 70%, 80%, 90%, 95%, 99% or 99.9% of their characteristics or properties. For example, a substantial level of elastic modulus, cohesiveness, tackiness, malleability or a biological activity of the cartilage matrix may be maintained during storage. The cartilage matrix may be optionally sterilized before storage. The modified cartilage (e.g., demineralized cartilage matrix) may be stored at an ambient room temperature (e.g., about 20-25° C.), cryopreserved or frozen.

The preparation method may further comprise drying the cartilage matrix. For example, the cartilage matrix may be freeze dried. The cartilage matrix may have a water activity (Aw) of less than about 0.5, 0.3 or 0.1.

FIG. 1 illustrates the preparation of a cartilage matrix according to one embodiment of the present invention. FIG. 1A shows six (6) preparation steps. Fresh or frozen cartilage tissues (e.g., articular, costal, septal, auricular and intervertebral cartilage) are recovered and then morecellized. In particular, the extracellular matrix (ECM) of the recovered cartilage tissues is particularized mechanically by, for example, manual sharp and blunt dissection, mechanical grinder, wet/dry mill or cryogenic mill. Decellularization may be added between tissue recovery and morcellization, and achieved by using a detergent with or without an endonuclease.

The morcellized cartilage tissues are then treated with cartilage particle deglycosylation and optionally demineralization (FIG. 1B). The particle demineralization may be achieved using acid treatment or chelating agents. The cartilage particle deglycosylation may be specific deglycosylation through use of a single or combination of tissue-derived, purified or recombinant glycolytic enzymes such as deglycosidase (e.g., PNGase F, O-glycosidase, neuraminidase, β 1-4 galactosidase, β-N-cetylglucosaminidase), endoglycosidases, hyaluronidases and chondroitinases. The cartilage particle deglycosylation may be non-specific deglycosylation through use of a single or combination of tissue-derived, purified or recombinant, proteolytic enzymes (e.g., Pepsin and Papain). The cartilage particle deglycosylation may be chemical deglycosylation by, for example, trichloroacetic acid, trifluoromethanesulfonic acid and hydrazine.

The treated cartilage tissues are then dehydrated by, for example, freeze-drying, critical point drying or lyophilization. Lastly, the dehydrated tissues are sterilized by, for example, gamma irradiation, e-beam processing, ethylene oxide (EtO), critical $CO_2$, or dry heat.

The term "about" as used herein when referring to a measurable value such as an amount, a percentage, and the like, is meant to encompass variations of ±20% or ±10%, ±5%, ±1%, or ±0.1% from the specified value, as such variations are appropriate.

Example 1. Preparation of Articular Demineralized Cartilage Matrix

Total knees were recovered from 20 consented human donors, processed separately, and used without prior freezing or kept frozen at −80° C. until further processing. Previously frozen knees were thawed in a refrigerator for 24 hrs prior to processing. The joints were disarticulated aseptically and the surrounding connective and soft tissues incl. tendons and synovial membranes were removed. Articular cartilage was isolated from all of the articular surfaces of the knee including the condyle, patella, and tibial plateau. The cartilage was separated from the underlying bone either by sharp incision using a scalpel or rasped off the bone using a grater. The cartilage was kept moist throughout isolation using sterile saline-soaked gauze. Grated cartilage pieces were used immediately, while larger pieces of cartilage were cut to pieces no larger than 1.0 $cm^2$. The cartilage pieces were rinsed three times in saline and decellularized at a 1:8 weight-to-volume ratio in decellularization solution containing a zwitter ionic detergent, 5.0 mg/mL 3-[(3-cholamidopropyl)dimethylammonio]-1-propanesulfonate (CHAPS), an endonuclease 50 U/mL benzonase, and antibiotics, 1,000 U/mL Polymycin, 50 μg/mL Vancomycin and 150 μg/mL Lincocin, for 16-24 hrs at 37° C. with agitation. Following decellularization, the mineralized cartilage matrix pieces were washed in sterile saline, frozen at −80° C., and comminuted to a fine particulate using a cryomill yielding particles no larger than 150 μm in diameter. The mineralized cartilage matrix particles were treated in a 1% Pepsin solution in 0.1N Hydrochloric Acid for up to 48 hrs under agitation and collected by centrifugation. The supernatant was discarded and the remaining demineralized cartilage matrix particles were frozen and freeze-dried. The resulting product was a disk of demineralized cartilage matrix. A subset of samples were terminally sterilized by gamma irradiation prior to rehydration.

The preparation of cartilage matrix for the formation of a cohesive putty was further evaluated using a specific deglycosylase treatment without additional particle demineralization (FIG. 1B). 1.0 g of mineralized cartilage matrix particles were treated in a solution containing 100 U/mL hyaluronidase under agitation for 48 hrs. The treated particles were collected by centrifugation and freeze-dried as described above.

The residual mineral content of the demineralized cartilage matrix was determined by spectrophotometric quantification. Briefly, cartilage samples were dried in an oven at 110° C. for greater than 30 minutes to remove any residual water and digested in 1.0M Hydrochloric Acid using the MARS XPRESS system (CEM Inc.). The samples' residual calcium concentration was measured spectrophotometrically using a Calcium Reagent Kit (Eagles Diagnostics) according to the manufacturer's protocol. A sample's calcium content was determined as its percentage in dry weight. The treatment of cartilage matrix particles with Pepsin under acidic conditions resulted in their demineralization to residual calcium levels below the level of detection while the mineralized cartilage matrix showed a calcium content of 0.58±0.03 (% dry weight).

Figure 3:
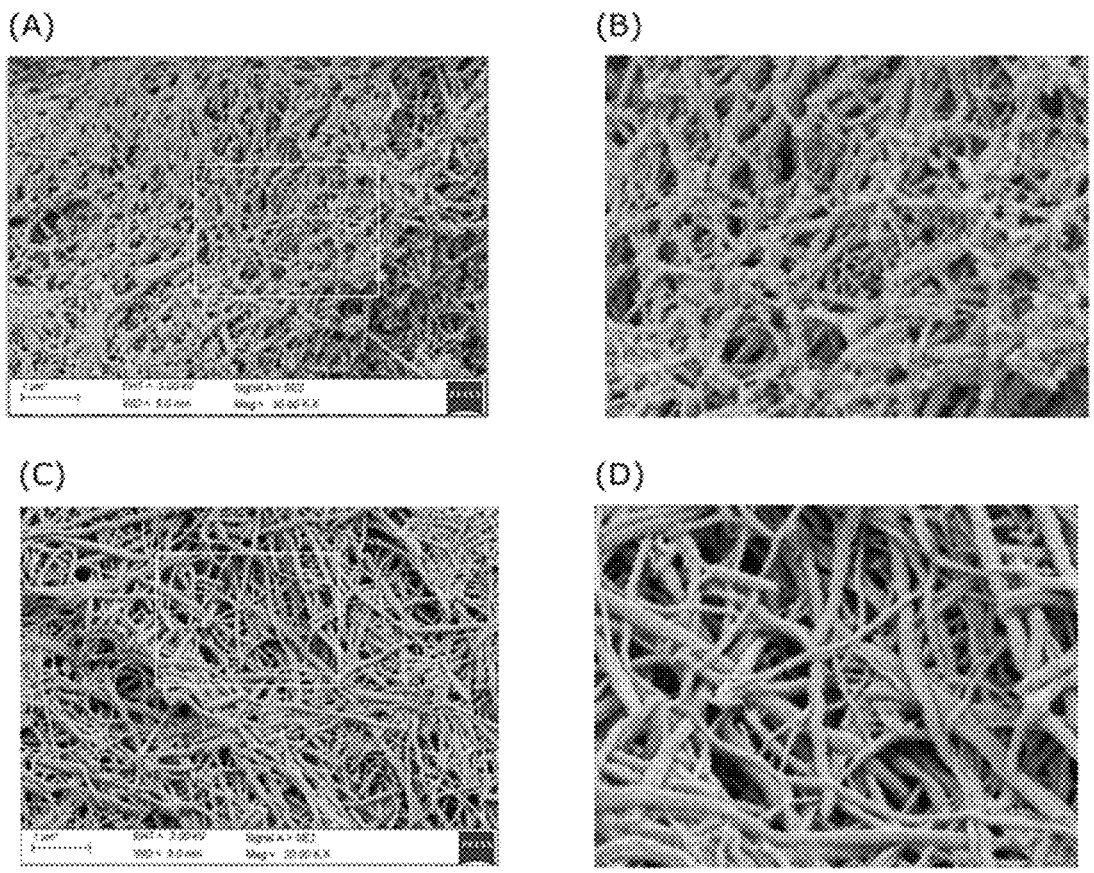
FIG. 3 shows surface characteristics of cartilage samples by scanning electron microscopy (SEM): collagen fibers in untreated, decellularized cartilage matrix (A and B) or treated decellularized cartilage matrix (C and D).

The cartilage samples' surface characteristics were determined by scanning electron microscopy (SEM). Briefly, a disk of mineralized or demineralized cartilage matrix was fractured manually. A piece from the center region was secured to an electron microscope mount and sputter coated in gold before imaging on a Zeiss Sigma VP field scanning electron microscope. The collagen fibers in the demineralized cartilage matrix were smooth in appearance (FIGS. 3B and 3D) while collagen fibers in non-treated decellularized cartilage matrix appeared rough (FIGS. 3A and 3C).

Figure 4:
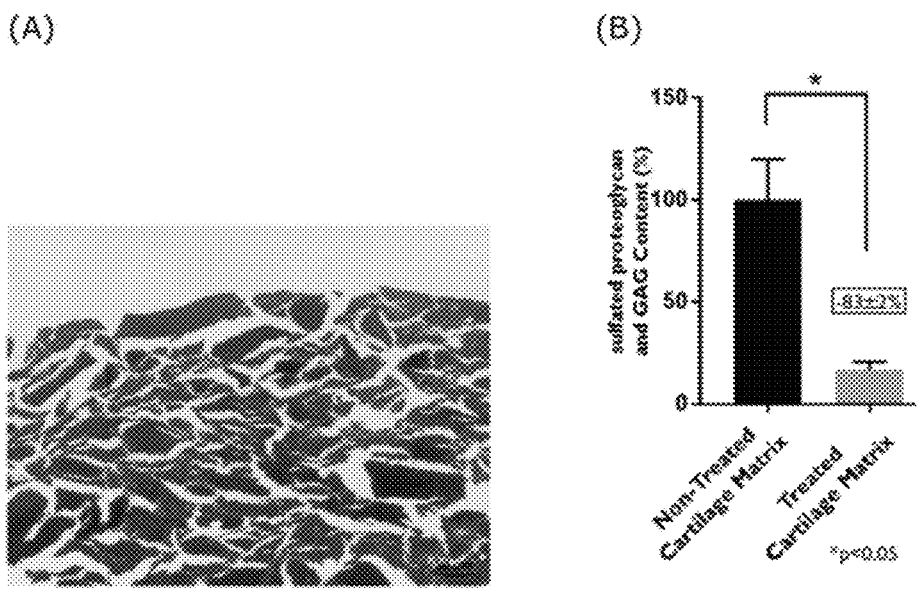
FIG. 4 shows (A) treated decellularized cartilage matrix particles following histological Safranin O staining, and (B) sulfated proteoglycan and glycosaminoglycan (GAG) content in untreated and treated cartilage matrix particles.

The cartilage samples' glycosaminoglycan (GAG) content and distribution were assessed by gross histology and biochemical assessments. For qualitative GAG assessments, paraffin-embedded cartilage samples were stained by conventional Safranin O staining (FIG. 4A). The presence of GAGs is indicated by the observation of a characteristic red staining pattern, while areas without significant GAG accumulation appear blue. Quantitative assessments of the sample's sulfated proteoglycan and GAG content was determined using the commercial Blyscan assay (Bicolor Inc.) according to the manufacturer's instructions. Briefly, cartilage samples were solubilized by digestion in Proteinase K for 3 hrs at 55° C. under agitation. The cartilage samples' content of sulfated proteoglycans and GAGs was determined spectrophotometrically to a known standard of chondroitin sulphate (FIG. 4B). The histological evaluation identified the absence of a characteristics red staining pattern in the Safranin O stained demineralized cartilage particles indicating their loss during processing. An 83±2% reduction in sulfated proteoglycans and GAGs in fully processed cartilage matrix particle was further confirmed by quantitative analysis.

Example 2. Preparation of Costal Demineralized Cartilage Matrix

Sterna including the neighboring costal cartilage were recovered from the rib cage of 2 consented human donors, processed separately, and kept frozen at −80° C. until further processing. The tissues were thawed in a refrigerator for up to 24 hrs prior to processing. The costal cartilage was separated from the sternum by sharp incision and freed from the surrounding connective tissue by mechanical separation.

The hyaline cartilage was cut into pieces no larger than 1.0 $cm^3$ and kept moist using sterile saline-soaked gauze. The cartilage pieces were rinsed three times in saline and decellularized in decellularization solution at 1:8 weight-to-volume ratio containing a zwitter ionic detergent, 5.0 mg/mL 3-[(3-cholamidopropyl)dimethylammonio]-1-propanesulfonate (CHAPS), an endonuclease, 50 U/mL benzonase, and antibiotics, 1,000 U/mL Polymycin, 50 μg/mL Vancomycin, 150 μg/mL Lincocin, for 16-24 hrs. Following decellularization, the mineralized cartilage matrix pieces were washed in sterile saline, frozen at −80° C., and comminuted to a fine particulate using a cryomill yielding particles no larger than 150 μm in diameter. The mineralized cartilage matrix particles were treated in a 1% Pepsin solution in 0.1N Hydrochloric Acid for up to 48 hrs and collected by centrifugation. The supernatant was discarded and the remaining demineralized cartilage matrix particles were frozen and freeze-dried. The resulting product was a disk of demineralized cartilage matrix.

Figure 5:
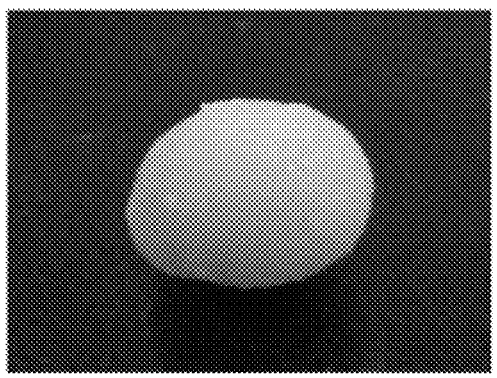
FIG. 5 shows treated cartilage matrix putty (A) in saline (B) subject to vigorous agitation (Vortex) (C), following vigorous agitation (Vortex) in saline (D), or injected from a syringe into water (E).
Figure 5:
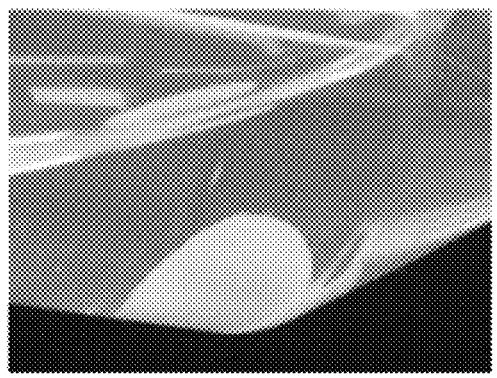
Figure 5:
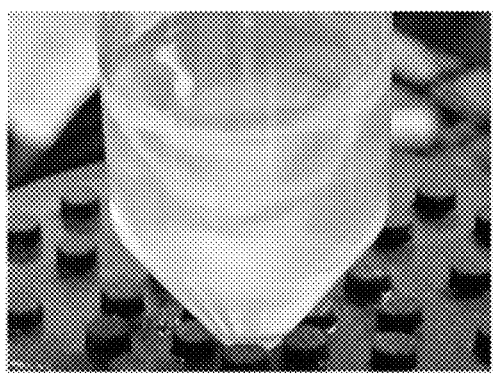
Figure 5:
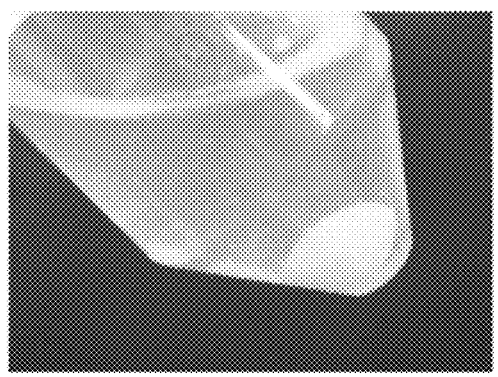
Figure 5:
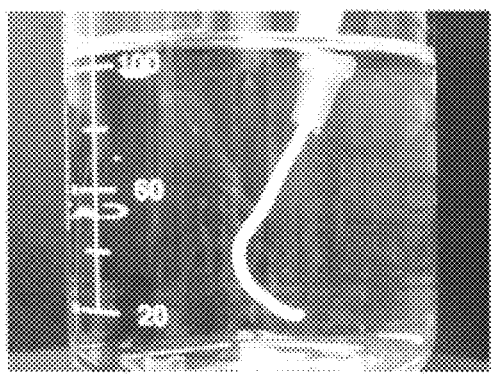

Example 3. Rehydration of Demineralized Cartilage Matrix—Preparation and Handling Assessment of Demineralized Cartilage Putty The demineralized cartilage matrix (FIG. 5A) was rehydrated with sterile water and mixed thoroughly by hand to yield a homogeneous 2.0 g/mL demineralized cartilage putty without apparent dry regions. The demineralized cartilage putty was tacky to the touch and could easily be shaped. All of the demineralized cartilage putties tested had similar handling characteristics irrespective of the cartilage's original tissue source. To test putty cohesiveness, mineralized and demineralized cartilage putties we directly submerged in water or injected into water via a plastic syringe. The demineralized cartilage matrix putty retained its shape when fully submerged in water (FIG. 5B) and even remained intact without fragmentation during vigorous mechanical agitation on a laboratory vortex mixer at 3200 rpm (FIGS. 5C and 5D). When delivered from a syringe into water, demineralized cartilage matrix putty extruded as a continuous structure that was not easily disrupted (FIG. 5E). Extruded and shaped demineralized cartilage matrix putty was retrieved from the water with minimal loss of material.

Figure 6:
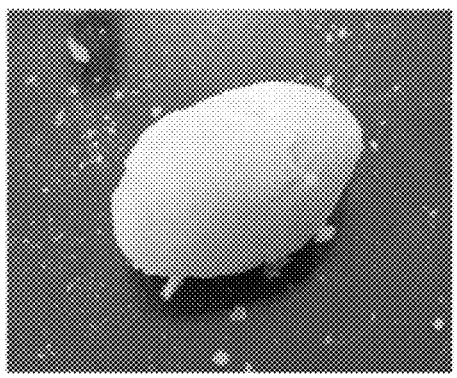
FIG. 6 shows a putty made from non-treated, mineralized cartilage matrix (A) in saline (B) or injected from a syringe into water (C).
Figure 6:
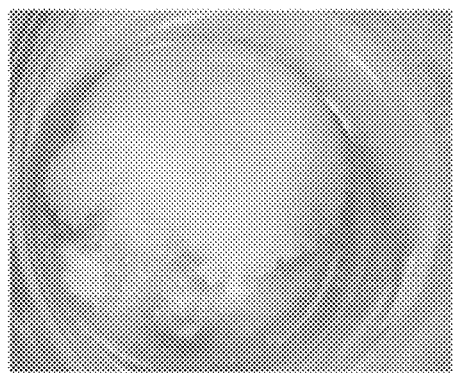
Figure 6:
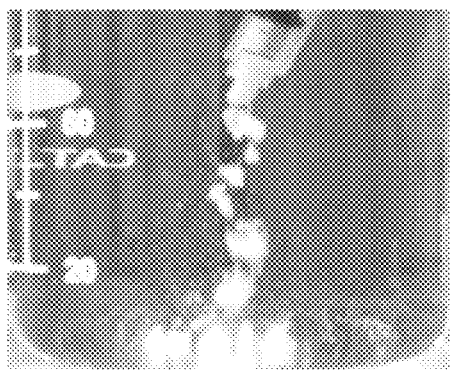

On the other hand, a putty made from freeze-dried, mineralized cartilage particles, i.e. particles that had not been treated according to the aforementioned protocol including decellularization and demineralization/deglycosylation, is only lightly cohesive to the touch and often stick to the surgical gloves rather themselves when manipulated. Mineralized cartilage putties were prepared at a 1.0 g/mL concentration to form a homogeneous putty without containing noticeable dry regions (FIG. 6A). This putty disintegrated almost instantaneously when fully submerged in water and did not withstand even gentle manipulation (FIG. 6B). Larger fragments could not be retrieved from the solution without falling apart. Similarly, mineralized cartilage putty fragments rapidly dispersed when injected into water (FIG. 6C).

Example 4. Texture Analysis of Cartilage Putties

Figure 7:
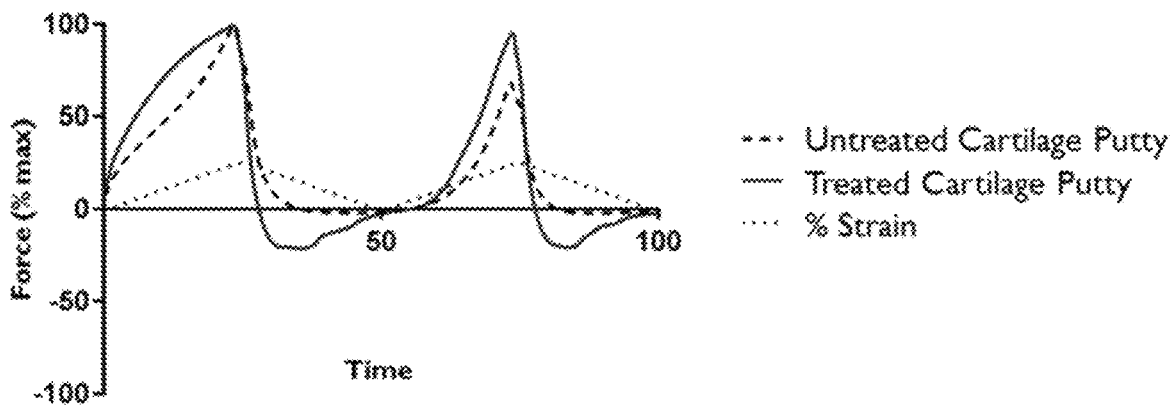
FIG. 7 shows texture profiles of cartilage putties made from untreated cartilage particles or treated cartilage particles (A), illustration of calculation of material cohesiveness, springiness, resilience, and adhesiveness from the force and strain data (B), and (C) mechanical profiles of a modeling compound and a surface wetted crystalline material.
Figure 7:
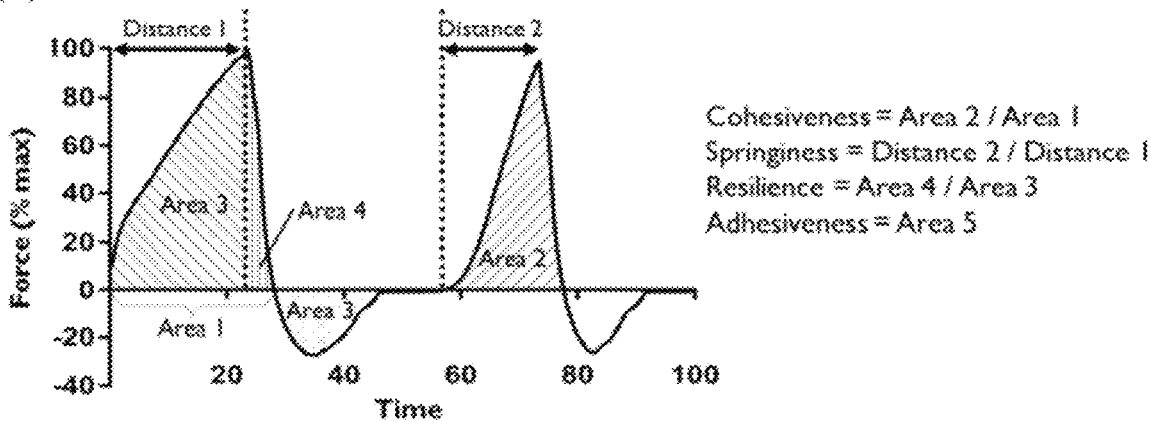
Figure 7:
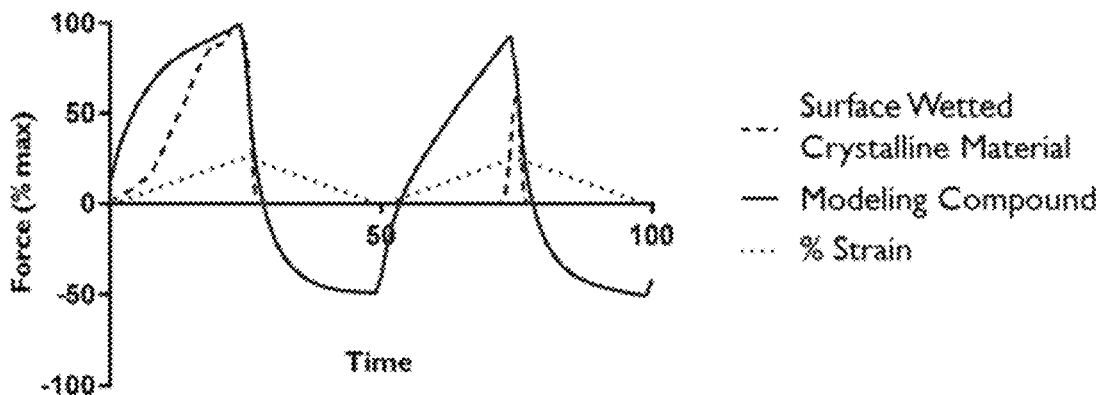

The mechanical profile of cartilage putties made from untreated cartilage particles and demineralized cartilage particles were compared based on texture profile analysis. Homogenous cartilage putty samples were prepared from non-treated, mineralized or demineralized cartilage matrix particles in sterile water and rolled out to a layer thickness of approximately 1.0 mm. A 10 mm bio-punch was used to create a circular test sample that was loaded onto the parallel plates of the Malvern Kinexus Lab+ rheometer featuring an 8 mm upper platen. A preload of 0.2 N in compression was placed on each sample, before undergoing 2 unconfined, compressive cycles to 25% compressive strain at 25° C. Force was measured throughout the test (FIG. 7A). Material cohesiveness, springiness, resilience, and adhesiveness (Table 1) were calculated from the force and strain data as illustrated (FIG. 7B). Putty cohesiveness was measured as a ratio of the amount of work absorbed in the second compressive cycle (FIG. 7B, Area 2) to the work of the first compressive cycle (FIG. 7B, Area 1). The area under the force curve indicates the work per compressive cycle. The demineralized cartilage matrix putty was more cohesive and adhesive than a putty made from untreated cartilage matrix particles alone. Most strikingly, the demineralized cartilage matrix putty was also 10 times more adhesive than a putty made form untreated cartilage particles as seen by the negative force values during the unloading phases in both the first and second cycle. The negative force results from the putty sticking to the parallel plates during the unloading process. In comparison to other more common materials, the cartilage matrix putty showed a similar texture profile to the one observed with common modeling compound, while untreated cartilage particles showed a profile that was similar to that observed for a surface wetted crystalline material (FIG. 7C).

TABLE 1

Mechanical profile of cartilage putties

| | Cohesiveness (%) | Springiness (%) | Resilience (%) | Adhesiveness (%) |
|---|---|---|---|---|
| Demineralized Cartilage Matrix Putty | 48.05 | 79.21 | 17.66 | −759.38 |
| Untreated Cartilage Putty | 41.46 | 74.00 | 31.51 | −75.56 |

Example 5. Rheological Behavior of Demineralized Cartilage Matrix Putty

Figure 8:
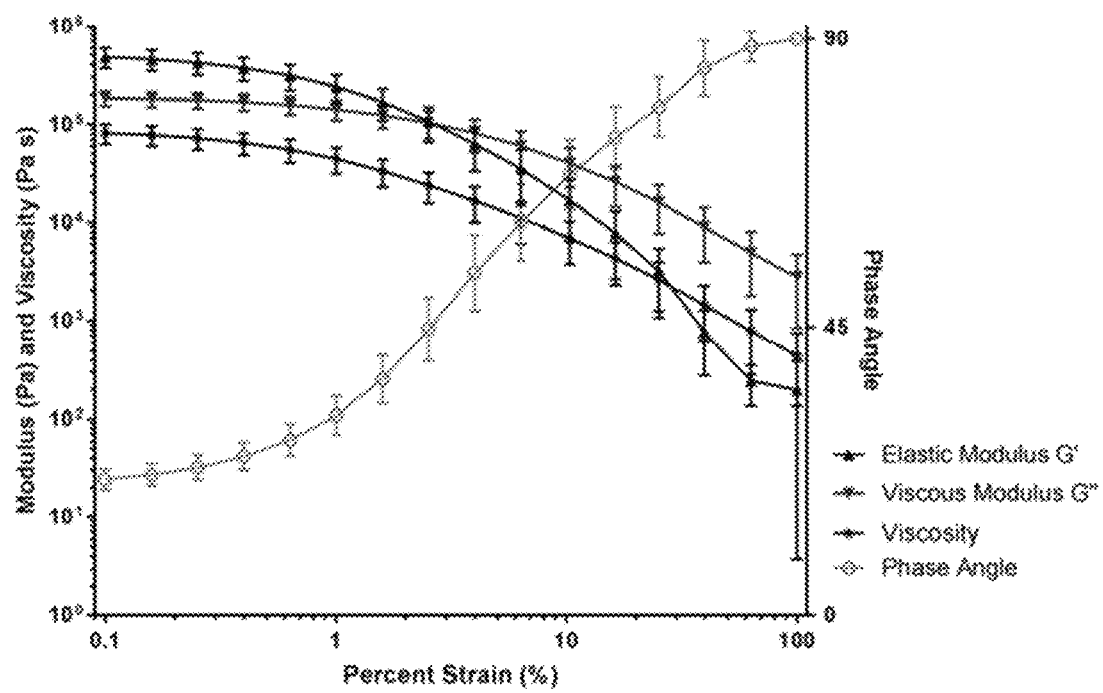
FIG. 8 shows the rheological properties of treated cartilage putty.

The demineralized cartilage matrix was rehydrated with sterile water and mixed thoroughly by hand to yield a homogeneous 2.0 g/mL demineralized cartilage matrix putty. The putty was rolled out to a layer thickness of approximately 3.0 mm. A 10 mm biopsy punch was used to create a circular test sample that was loaded onto the parallel plates of the Malvern Kinexus Lab+ rheometer featuring an 8 mm upper platen. The sample was equilibrated at 37° C. for 5 minutes before the initiation of a shear strain sweep at 1 Hz (results are displayed as the reported average from two test replicates from two separate cartilage matrix putty preparations). The cartilage matrix putty showed a shear thinning behavior with increasing shear strain rates (FIG. 8). The material displayed a more solid like behavior at strains of less than 2.5% as indicated by an increased elastic modulus, low phase angle, and viscosity. At shear strains larger than 2.5%, the putty behaved more like a fluid with phase angles greater than 45 degrees and a decrease in sample viscosity.

Figure 9:
FIG. 9 shows an irregularly-shaped treatment site on the articular surface of a medial human cadaveric condyle before (A) or after (B) applying treated cartilage matrix putty directly to a defect in an open resurfacing procedure.
Figure 9:
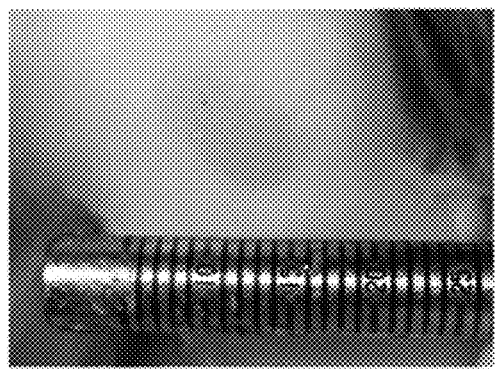

Example 6. Use of Demineralized Cartilage Matrix Putty in Open and Fully Arthroscopic Joint Resurfacing Applications The use of demineralized cartilage matrix putty for joint resurfacing applications was assessed in human cadaveric wet lab simulation by a conventional open procedure and a fully arthroscopic approach without creation of an access portal or opening of the joint. An irregularly-shaped treatment site measuring 0.6×0.4 cm was created on a disarticulated human medial condyle by debriding the articular cartilage using an arthroscopic curette in an open procedure ensuring the formation of a clean bone bed and stable edges of the surrounding cartilage. The 2.0 g/mL demineralized cartilage matrix putty was applied directly to the defect and manually smoothed over to shape the surface characteristics of the repair. The repair resulted in a satisfying repair and complete filling of the cartilage defect (FIG. 9).

Figure 10:
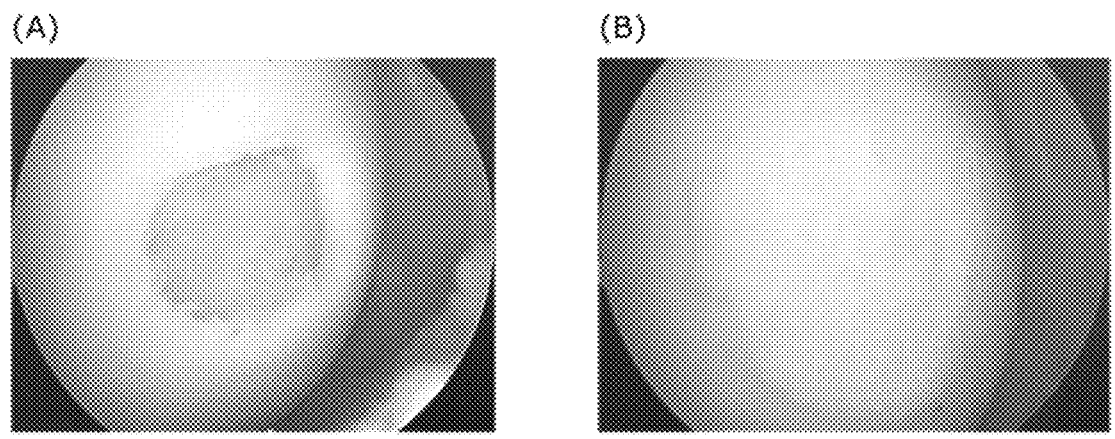
FIG. 10 shows a treatment site on the articular surface of a medial human cadaveric condyle before (A) or after (B) applying treated cartilage matrix putty directly to a defect in a closed, fully arthroscopic joint resurfacing procedure.

The potential use of demineralized cartilage matrix putty in a fully arthroscopic joint resurfacing procedure was simulated in a second human cadaveric wet lab. The putty was applied arthroscopically under aqueous conditions without the placement of an additional skin incision (mini-arthrotomy) or drainage of joint fluid though one of the access ports. A 1.5 cm² cartilage defect was created on the medial condyle using an arthroscopic curette ensuring the formation of a clean bone bed and stable edges of the surrounding cartilage. The trocar was kept closed to prevent air from entering the joint and ensure a fully closed procedure. Tissue debris was removed with an arthroscopic dissector. Demineralized cartilage matrix putty was applied directly to the defect using a syringe and smoothed over with an arthroscopic spatula. The arthroscopic instruments and viewing scope were removed and the joint was mobilized vigorously through 20 cycles of complete articulation with manual forced loading. The demineralized cartilage matrix putty remained in place throughout mobilization and did not display signs of fragmentation or delamination from the subchondral bone or neighboring cartilage (FIG. 10).

Figure 11:
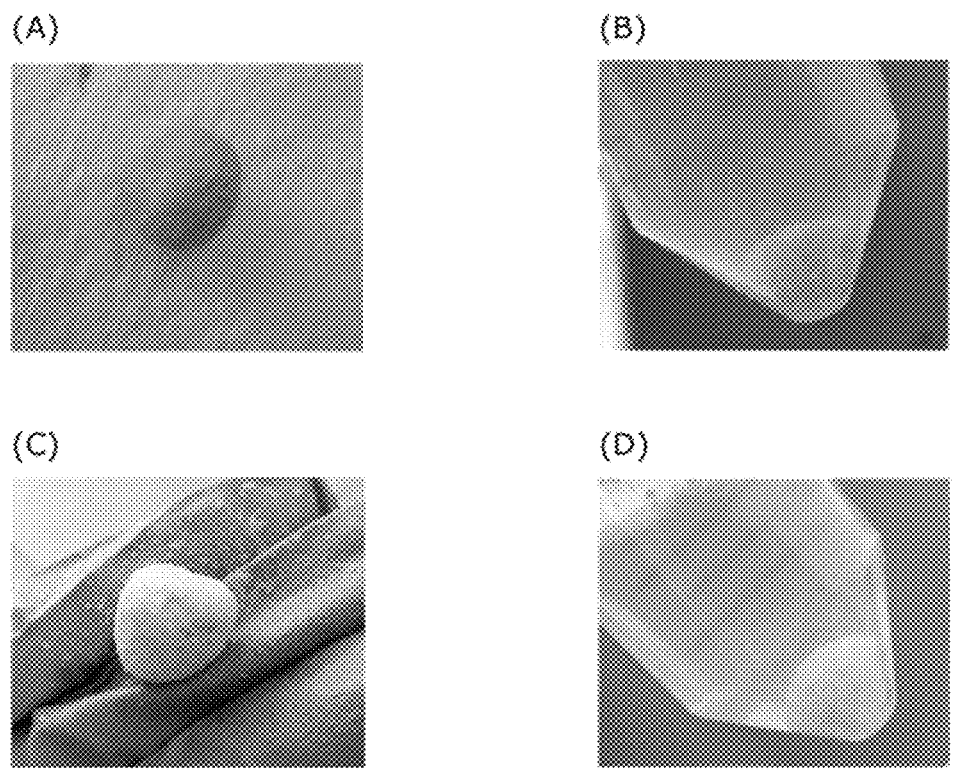
FIG. 11 shows 90% (A and B) or 75% (C and D) by weight of viable cartilage particles in treated cartilage matrix putty based on total weight of the mixture before (A and C) and after (B and D) vigorous agitation.
Figure 12:
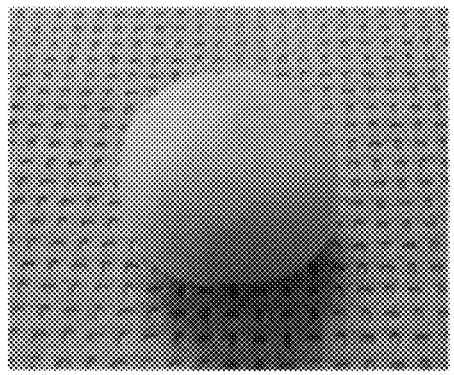
FIG. 12 shows 5% (A), 40% (B) and 70% (C) of a demineralized bone matrix in a demineralized cartilage matrix by weight based on total weight of the mixture.
Figure 12:
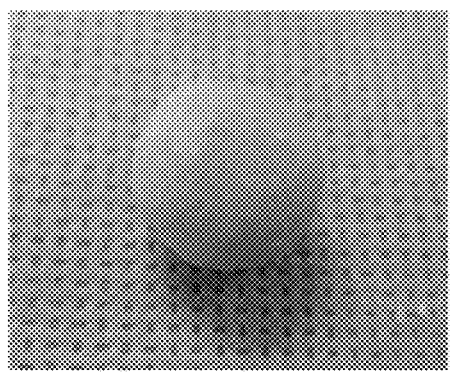
Figure 12:
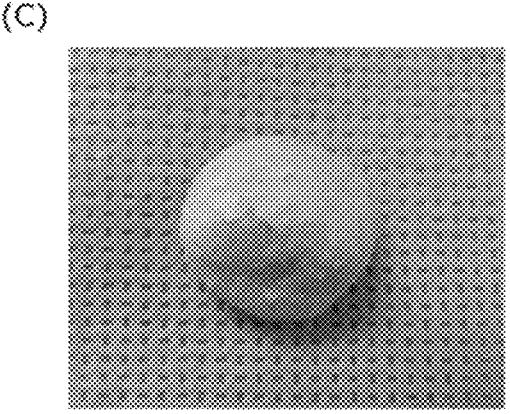

Example 7. Use of Demineralized Cartilage Matrix Putty as Carrier for the Delivery of Fresh Cartilage Pieces and Tissue-Derived Matrices The potential use of the demineralized cartilage matrix putty as carrier for the delivery of tissue-derived matrices and fresh cartilage fragments was assessed using Demineralized Bone Matrix (DBM) particles and fresh non-treated articular cartilage particles. Demineralized cartilage matrix putty was mixed with fresh, mineralized cartilage particles at increasing ratios of up to 90% fresh cartilage by weight. Resulting mixtures retained the cohesive properties and handling properties of demineralized cartilage matrix putty (FIG. 11A). Putties further remained intact following vigorous agitation on a laboratory vortex mixer similar to that described for the cartilage matrix putty alone (FIG. 11B). In a separate set of experiments, demineralized cartilage matrix putty was mixed with DBM at increasing ratios of up to 70% DBM by weight (FIGS. 11C and 11D). The resulting mixtures retained a similar level of cohesiveness and malleability to demineralized cartilage matrix putty (FIG. 11), but displayed an increasing degree of granularity due to the increase in DBM particles (FIG. 12).

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. An implant comprising a composition, wherein the composition comprises a cartilage matrix putty comprising dehydrated, deglycosylated, decellularized cartilage matrix particles and water, wherein the cartilage matrix putty is prepared according to a method comprising:
   (a) incubating a cartilage in a decellularization solution comprising a detergent, whereby a decellularized cartilage matrix is generated in the form of particles;
   (b) deglycosylating the decellularized cartilage matrix particles, comprising treating the particles with a deglycosylation solution comprising a glycolytic enzyme, a proteolytic enzyme, an acid, hydrazine, or a combination thereof, and dehydrating the deglycosylated, decellularized cartilage matrix particles; and
   (c) rehydrating the dehydrated, deglycosylated, decellularized cartilage matrix particles with a solution comprising water to yield a homogenous cartilage matrix putty;
   wherein the cartilage matrix putty is cohesive, and wherein cohesive is defined as:
   when a sample of the cartilage matrix putty consisting of the dehydrated, deglycosylated, decellularized cartilage matrix particles and 1 mL water per 2 grams of the dehydrated, deglycosylated, decellularized cartilage matrix particles is placed in an aqueous environment the sample of the cartilage matrix putty retains at least 95% of its weight after 180 minutes in the aqueous environment.

2. The implant of claim 1, wherein the cartilage is selected from the group consisting of an articular cartilage, a costal cartilage, an auricular cartilage, and a nasal cartilage.

3. The implant of claim 1, further comprising cartilage particulates.

4. A package comprising the implant of claim 1.

5. A package comprising the implant of claim 3.

6. A method of treating a tissue or organ defect in a subject, comprising placing the implant of claim 1 at the tissue or organ defect.

7. A method of treating a tissue or organ defect in a subject, comprising placing the implant of claim 3 at the tissue or organ defect.

8. The implant of claim 1, wherein the particles have a diameter no greater than 150 μm.

9. The implant of claim 1, wherein the deglycosylation solution comprises pepsin.

10. The implant of claim 1, wherein the deglycosylation solution has a pH lower than 2.

11. The implant of claim 1, wherein the acid is trichloroacetic acid or trifluoromethanesulfonic acid.

12. The implant of claim 1, whereby the dehydrating comprises freeze-drying.

13. The implant of claim 1, wherein the decellularization solution further comprises an endonuclease.

14. The implant of claim 1, wherein the deglycosylated, decellularized cartilage matrix particles have been treated to within 10-300 μm from the surface of the deglycosylated, decellularized cartilage matrix particles.

15. The implant of claim 1, wherein the deglycosylated, decellularized cartilage matrix particles have a specific surface area of from about 20-20,000 cm²/g.

16. The implant of claim 1, wherein the deglycosylated, decellularized cartilage matrix particles comprise less than about 6 wt % of calcium based on the dry weight of the deglycosylated, decellularized cartilage matrix particles.

* * * * *

UNITED STATES PATENT AND TRADEMARK OFFICE
CERTIFICATE OF CORRECTION

| | | |
|---|---|---|
| PATENT NO. | : 12,419,992 B2 | Page 1 of 1 |
| APPLICATION NO. | : 16/631942 | |
| DATED | : September 23, 2025 | |
| INVENTOR(S) | : Alexander Huber | |

It is certified that error appears in the above-identified patent and that said Letters Patent is hereby corrected as shown below:

On the Title Page

Item (73) Assignee, Please change "Matney Legal Group PLLC" to --LifeNet Health--.

Signed and Sealed this
Fourth Day of November, 2025

John A. Squires
*Director of the United States Patent and Trademark Office*